United States Patent [19]

DeCote

[11] Patent Number: 4,674,508
[45] Date of Patent: Jun. 23, 1987

[54] LOW-POWER CONSUMPTION CARDIAC PACER BASED ON AUTOMATIC VERIFICATION OF EVOKED CONTRACTIONS

[75] Inventor: Robert DeCote, Miami, Fla.
[73] Assignee: Cordis Corporation, Miami, Fla.
[21] Appl. No.: 738,605
[22] Filed: May 28, 1985
[51] Int. Cl.⁴ .............................................. A61N 1/36
[52] U.S. Cl. .............................. 128/419 PT; 128/697
[58] Field of Search .................... 128/419 PG, 419 PT

[56] References Cited

U.S. PATENT DOCUMENTS

| | | | |
|---|---|---|---|
| 3,757,790 | 9/1973 | Herrmann | 128/419 PT |
| 3,777,762 | 12/1973 | Nielsen | 128/419 PT |
| 3,800,801 | 4/1974 | Gaillard | 128/419 PT |
| 4,055,189 | 10/1977 | Auerbach et al. | 128/419 PG |
| 4,114,627 | 9/1978 | Leuyn et al. | 128/419 PG |
| 4,181,133 | 1/1980 | Kolgnik et al. | 128/419 PG |
| 4,228,803 | 10/1980 | Rickards | 128/419 PG |
| 4,245,643 | 1/1981 | Benzing et al. | 128/419 PT |
| 4,290,430 | 9/1981 | Bihn et al. | 128/419 PT |
| 4,337,776 | 7/1982 | Daly et al. | 128/419 PT |

*Primary Examiner*—William F. Kamm
*Attorney, Agent, or Firm*—Lockwood, Alex, FitzGibbon & Cummings

[57] ABSTRACT

A low-power consumption implantable pacer includes a system for detecting evoked cardiac contractions in which pacing pulses are initially applied to a patient's heart in pairs such that at most only one pulse of a pair can induce capture. The lead recovery waveforms produced in response to each of the pulses of a pair are detected and compared. By selectively varying the pulse energy level, the patient's capture threshold is determined. Pulse energy is then increased such that the first pulse of each pair induces capture and the lead recovery waveform resulting from the second, non-capturing pulse is stored. To conserve battery current, single pacing pulses are then supplied to the heart, and the lead recovery waveforms developed by the single pulses are compared against the stored waveform to yield a reference difference signal which verifies capture. When a significant change in difference signals is detected, the pacer automatically repeats the foregoing paired-pulse autocapture threshold determination and output level adjustment algorithm.

13 Claims, 4 Drawing Figures

U.S. Patent   Jun. 23, 1987   Sheet 1 of 3   4,674,508
FIG. 1
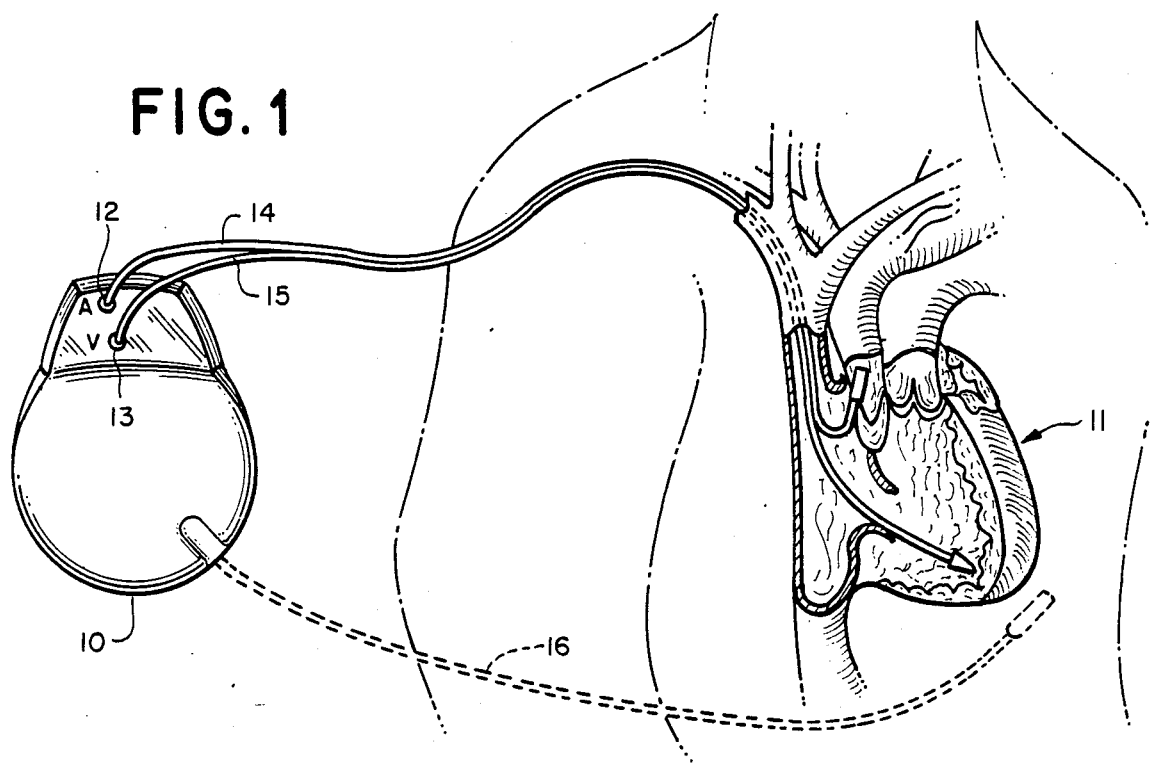
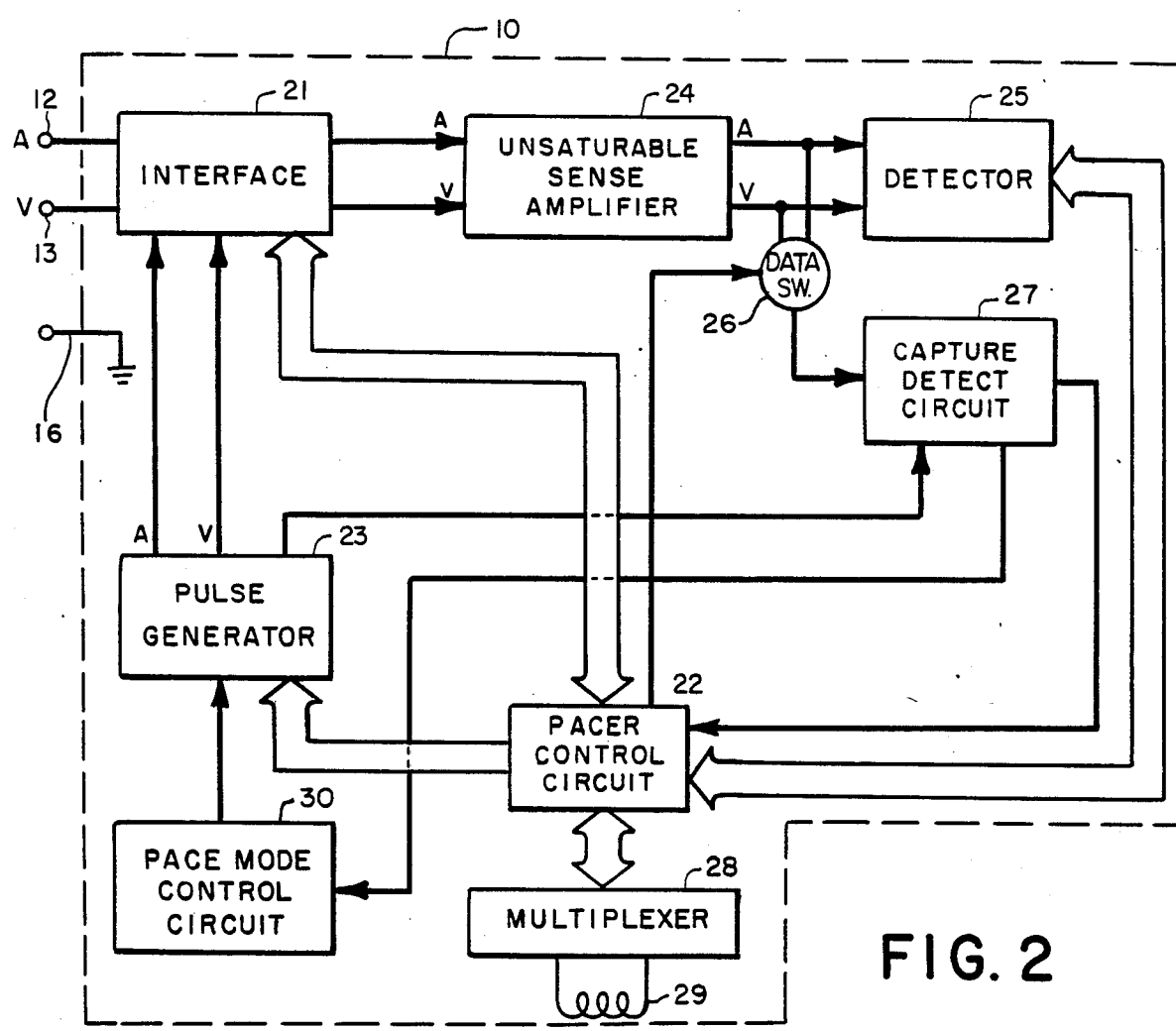
FIG. 2

LOW-POWER CONSUMPTION CARDIAC PACER BASED ON AUTOMATIC VERIFICATION OF EVOKED CONTRACTIONS

BACKGROUND OF THE INVENTION

This invention relates generally to cardic pacers having systems for automatically determining the minimum pacing pulse energy required to reliably stimulate a patient's heart, and more particularly to an improved system for use in such pacers wherein the detection of induced cardiac contractions is accomplished with reduced battery current drain.

The minimization of battery current drain in cardiac pacers is an important consideration in the design and operation of such devices. This is particularly true in the case of implantable pacers wherein premature battery failure necessitates invasive battery replacement surgery. Various improvements have therefore been made in cardiac pacer design and operation which seek to reduce battery current drain while nevertheless maintaining a high degree of pacing reliability.

One such improvement is described in the copending application Ser. No. 738,606, of the present inventor entitled "Cardiac Pacer Incorporating Means for Periodically Determinating Capture Threshold and Adjusting Pulse Output Level Accordingly". As described therein, a cardiac pacer is equipped with a system for automatically determining the minimum pacing pulse energy required to reliably stimulate a patient's heart. Once this level, known as the patient's capture threshold, is determined, pacing pulses at a fixed increment above the threshold level are generated and applied to the heart. Thereafter, single pacing pulses are provided. Periodically, the capture threshold is re-determined and the pacing pulse energy reset in accordance therewith. This permits the pacer to operate slightly above the actual capture threshold level without sacrificing pacing reliability and results in a significant reduction in battery current drain.

In such a pacer, pacing pulses are initially generated and applied to the heart in pairs while the cardiac response waveforms produced by each pulse of pair are compared in order to detect any signal components indicative of induced contractions. Upon the passage of a predetermined period of time, paired pulses are once again produced and the capture threshold is re-determined. While the ability to operate the pacer slightly above a patient's actual capture threshold significantly reduces battery current drain, the need to periodically re-determine capture threshold in itself wastes battery power if in fact no change in capture threshold has occurred. Also, pacing reliability could be compromised if capture threshold changes significantly during the single pulse time period.

The present invention is directed to an improvement in the above-described pacer which results in greater pacing reliability and possibly a further reduction in battery drain. This is accomplished by means of an improved capture detection system which effectively verifies induced cardiac contractions through use of a single pacing pulse and which redetermines capture threshold only when necessary. By eliminating the need for unnecessary paired-pulse redeterminations of capture threshold, substantial reduction in battery current is realized while the capability of continually verifying induced contractions improves the overall reliability of the pacer.

In view of the foregoing, it is a general object of the present invention to provide a new and improved low power consumption system for detecting evoked cardiac contractions.

It is a further object of the present invention to provide an improved cardiac pacer in which battery current drain is minimized.

It is still a further object of the present invention to provide a cardiac pacer in which capture is verified through use of a single applied pacing pulse and in which capture threshold is re-determined only when necessary.

SUMMARY OF THE INVENTION

A system for detecting cardiac contractions in response to application of pacing pulses to a patient's heart includes means for generating a series of pacing pulses. The pulse generating means are operable to provide single pacing pulses or to provide paired pacing pulses wherein each pair is formed by two individual pacing pulses spaced in time by less than the refractory period of the patient's heart. Means are provided for detecting the electrical artifact, indicative of any induced cardiac response event, produced in response to each of the pulses within a pulse pair applied to the patient's heart. In addition, means are provided for storing the electrical artifact developed by a pulse, within a pair, which did not induce a cardiac event. Once such an artifact is acquired, the pulse generating means are conditioned to develop single pacing pulses after which the artifacts produced in response to each of the subsequent single pacing pulses are compared against the stored artifact to yield a difference signal indicative of any cardiac event induced thereby.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 1 is a perspective view of a cardiac pacer constructed in accordance with the invention shown in conjunction with a patient's heart.

FIG. 2 is a simplified functional block diagram of the pacer illustrated in FIG. 1 showing the principal subsystems thereof.

DESCRIPTION OF THE PREFERRED EMBODIMENT

Figure 3:
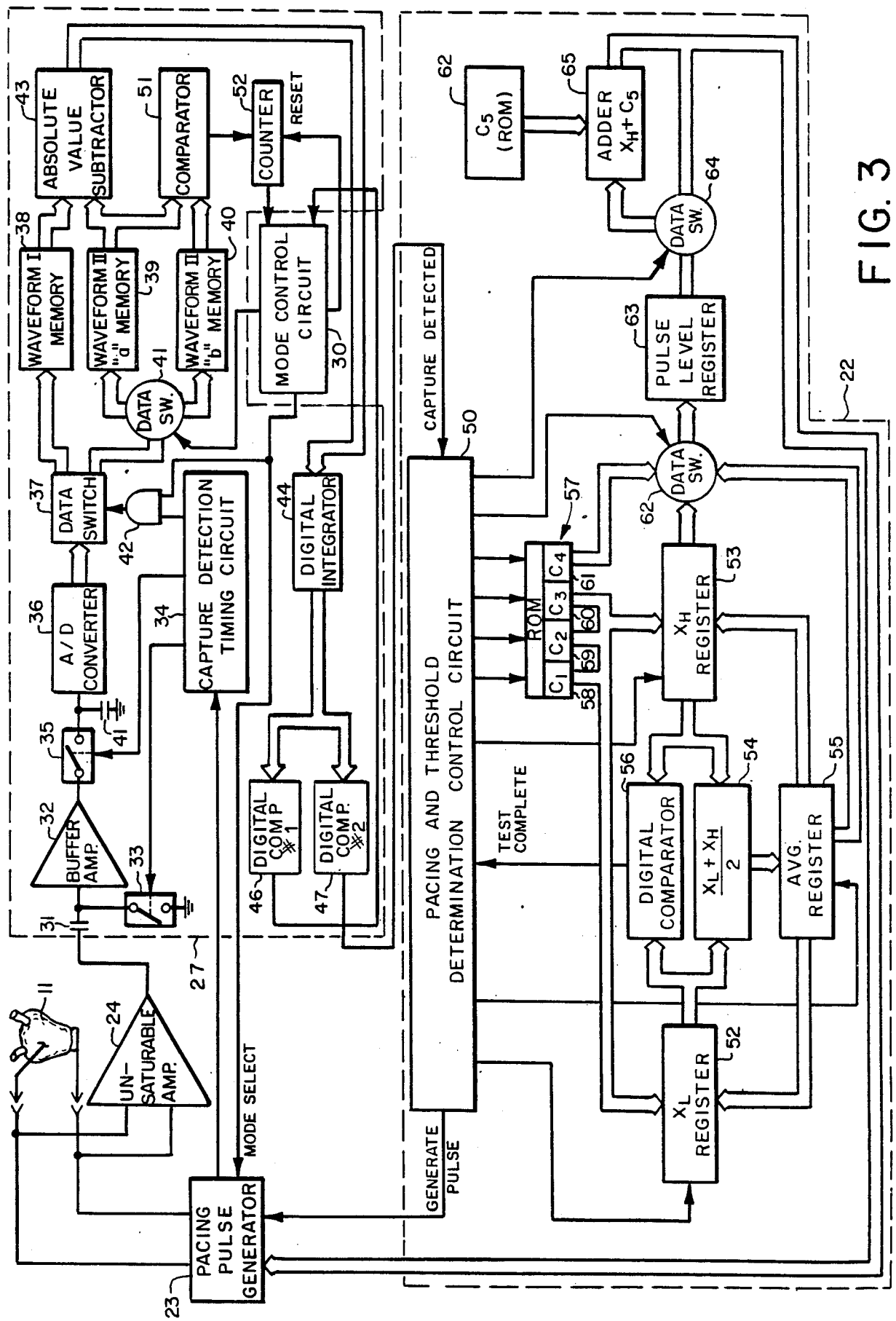
FIG. 3 is a simplified block diagram of an improved system for determining a patient's capture threshold incorporated in the pacer of FIG. 1.

Referring to the Figures, and in particular to FIG. 1, a battery operated implantable programmable cardiac pacer 10 constructed in accordance with the invention is shown in conjunction with a patient's heart 11. Pacer 10 develops atrial and ventricular pacing pulses which are made available at respective atrial and ventricular output terminals 12 and 13. Terminals 12 and 13 are connected, respectively, to the proximal ends of atrial and ventricular pacing leads 14 and 15 of known construction, the distal ends of which have been implanted in the atrial and ventricular myocardial tissue in known manner. An additional electrode 16, which although shown as a separate lead in FIG. 1, may comprise an electrically conductive surface on the pacer housing, provides an anodic reference for the atrial and ventricular cathode terminals. Pacer 10 is preferably formed as a self-contained and hermetically sealed device such that its operation is unaffected by exposure to body fluids.

Referring to FIG. 2, atrial and ventricular output terminals 12 and 13 are individually connected to an interface circuit 21 wherein appropriate connections are established between the pacing leads and the sensing and pacing circuitry of the pacer in accordance with a user-selected operating mode. Interface 21 operates under the control of a pacer control circuit 22 to establish the appropriate interconnections. A pulse generator 23, also under control of the pacer control circuit, generates atrial and ventricular pacing pulse sets which are applied through interface circuit 21 to the atrial and ventricular output terminals 12 and 13.

Pacer 10 further includes two channel unsaturable sense amplifier 24 for amplifying atrial and ventricular cardiac response signals which are sensed by the atrial and ventricular pacing leads 14 and 15 and are applied to the respective inputs of the sense amplifier under the direction of the pacer control circuit 22. Unsaturable sense amplifier 24, which is described in the concurrently filed copending application Ser. No. 738,608, of the present inventor entitled "Unsaturable Cardiac Sense Amplifier", is not driven into saturation by applied pacing pulses and is therefore capable of sensing and amplifying cardiac response signals developed immediately following the application of each pacing pulse. The outputs of sense amplifier 24 are coupled to a cardiac activity detector circuit 25 which, in known manner, detects naturally occurring cardiac contractions and allows the pacer to operate in a well known "demand" mode wherein pacing pulse are generated and applied to the heart only when the naturally occurring heart rate falls below a predetermined value.

In accordance with one aspect of the invention, the outputs of the unsaturable sense amplifier are synchronously coupled through a two-position data switch 26 to a capture detect circuit 27 which operates to detect cardiac contractions induced by pacing pulses applied to the heart. Data switch 26 operates under the control of the pacer control circuit 22 such that the atrial and ventricular outputs of sense amplifier 24 are sequentially coupled to capture detect circuit 27. The capture detect circuit 27 operates in conjunction with the pulse generator 23 and provides a capture indicative control signal to pacer control circuit 22 upon each detection of an induced cardiac contraction.

In accordance with conventional practice, pacer 10 is capable of operation in either the aforementioned "demand mode", or in a "free running" mode wherein pacing pulses are continually generated and applied to the heart at a predetermined rate. The addition of the capture detect circuit 27 allows operation in either mode such that the patient's capture threshold is automatically determined and pacing pulse level is automatically adjusted in accordance with the capture threshold so determined. Thus, pacing pulse level will change automatically in the event of a change in the capture threshold and will not require manual readjustment. User selection of the desired operating mode is provided by means of a multiplexer 28 and pickup element 29 which are coupled to pacer control circuit 22 by known means. Appropriately coded magnetic or radio frequency control signals are coupled to the pickup element 29 in known manner to provide user-selection of the operating mode from a remote external location.

In further accordance with the invention, pacer 10 includes a pace mode control circuit 30 coupled to both the capture detect circuit 27 and pulse generator 23. Pace mode control circuit 30, in response to an appropriate control input from capture detect circuit 27, conditions pulse generator 23 to develop pacing pulse sets which individually consist of either single or paired pacing pulses.

Capture detect circuit 27 operates, in part, in accordance with the principle, described in detail in the present inventor's copending application Ser. No. 738,607, entitled "System and Method for Detecting Evoked Cardiac Contractions", filed concurrently herewith, that if pacing pulses are applied to the heart in pairs, and if the pulse spacing within a pair is less than the refractory period of the heart, then, at most, only one pulse of the pair can induce cardiac capture. It has been experimentally determined that when the myocardium depolarizes, it becomes refractory for at least 150 milliseconds. Accordingly, pacing pulses generated in pairs spaced by a nominal 100 millisecond interval should, when applied to the heart, produce at most one contraction per pulse pair.

The operation of the capture detect circuit 27 is further based on the observation that post-pulse lead recovery artifacts are essentially completely decayed within 50 milliseconds following the end of each pacing pulse. Accordingly, the lead recovery artifact waveforms produced in response to each pulse of an identical pulse pair will be essentially identical in the absence of any induced cardiac response event. Thus, a properly implemented waveform subtraction of the lead recovery curves will yield a near-zero result in the event neither pulse of a pair induces capture. However, if either pulse induces a contraction of the heart, subtraction of the lead recovery curves will produce a detectable waveform difference. Since contraction on both pulses of a pair is an impossible condition, it follows that an induced cardiac contraction will always result in a non-zero waveform difference.

The operation of the improved capture detection system is based on the recognition that if the pulse energy level is increased somewhat above the actual capture threshold energy level, then it will be the first pulse of each pair which induces the resulting cardiac contraction. Accordingly, the second pulse of each pair, which will not produce a contraction, will essentially replicate the lead recovery waveform artifact developed by the cardiac pacing lead itself. Since this characteristic of the pacing lead does not change significantly except over a long period of time, it is not necessary to continue generating pacing pulses in pairs once a representative sample of the lead response waveform has been acquired and stored.

In order to activate the capture detection function, it is necessary that the pacer control circuit 22 and pacing pulse generator 23 initially function to develop paired pacing pulses for application to the heart. Typically, each pulse pair consists of two identical pulses spaced in time by less than the refractory period of the heart, while the interval between the pulse pairs is sufficient to provide repetition rates of between 40 and 120 pairs per minute.

As illustrated in FIG. 3, the outputs of dual-channel unsaturable amplifier 24 are synchronously applied to the capture detect circuit 27 along with a control output from pacing pulse generator 23. The selected output of amplifier 24 is coupled through a capacitor 31 to the input of buffer amplifier 32. The input of buffer amplifier 32 is also connected through a voltage controled analog switch 33 to circuit ground. A control voltage for controlling the operation of the analog switch is developed by a capture detection timing circuit 34 which develops a series of additional control voltages for controlling the operation of the capture detection circuit.

The output of buffer amplifier 32 is connected through a second voltage controlled switch 35 to the input of an analog-to-digital converter (ADC) 36. A capacitor 41 is connected between the input of ADC 36 and circuit ground, and, together with switch 35, forms a sample and hold circuit having a sampling frequency determined by the capture detection timing circuit 34.

Capacitor 31 and analog switch 33 form a gated clamp which operates under the control of the capture detection timing circuit 34. Switch 33 closes when a LOGIC-HIGH gated clamp control signal is developed by the capture detection timing circuit, and opens when the gated clamp control voltage is LOGIC-LOW.

The timing of the gated clamp control signal is such that switch 33 is made to close during a period beginning just before each output pacing pulse an terminating a few milliseconds after the completion of each pulse. The effect of this switching action is that the heaviest pacer pulse artifacts are thereby squelched. While switch 33 is closed, capacitor 31 will be charged to the output voltage of amplifier 24. Accordingly, immediately after the switch opens, the input to the buffer amplifier 32 will consist of the instantaneous output of the unsaturable amplifier 24 offset by the voltage to which capacitor 31 has been charged at the instant the switch opens. This assures that the initial voltage applied to the input of buffer amplifier 32 will be equal to ground potential, and any subsequent change in the output voltage of unsaturable amplifier 24 will appear as an identical change relative to ground at the input of the buffer amplifier. This function of the gated clamp serves to assure that the full dynamic range of ADC 36 is utilized since no matter what the actual output voltage of sense amplifier 24 is, the input voltage to buffer amplifier 32 will initially be zero volts and will then change from that potential in accordance with any subsequent change in the sense amplifier output voltage.

During the period in which analog switch 33 is open, the output of buffer amplifier 32 is converted to a series of digitally encoded data words by means of switch 35, capacitor 41 and ADC 36. The sampling rate, determined by the capture detection timing circuit 34, is selected so as to provide an accurate digital representation of the output of the buffer amplifier. Thus, each of the lead response waveforms, produced in response to each pulse of a pulse pair, will be converted to a corresponding series of digital bytes.

The output of ADC 36 is coupled to a two-position data switch 37 which operates under the control of the capture detection timing circuit 34. In one position, data switch 37 couples the output of ADC 36 directly to the input of a first waveform memory 38. In the other position, the ADC output is coupled through a second two-position data switch 41 operating under the control of the mode control circuit 30, to either of two additional waveform memories 39 and 40. The control voltage for controlling data switch 37 is developed by the capture detection timing circuit 34 and is applied to the control electrode of the switch through a two-input AND gate 42. The remaining input of the AND gate is connected to the mode control circuit 30 which can thereby inhibit operation of data switch 37 by means of an appropriate control voltage applied to gate 42.

The outputs of waveform memories 38 and 39 are coupled to the inputs of a digital absolute value subtractor 43 which performs a byte-by-byte comparison of the digital waveform representations stored in each of the memories. Subtractor 43 provides a digital signal indicative of the absolute difference between the waveforms stored in memories 38 and 39. The difference signal thus generated is coupled to a digital integrator 44 the output of which is coupled to a pair of digital comparators 46 and 47.

Digital integrator 44 integrates the digital difference signal from absolute value subtractor 43 over time, while the digital comparators 46 and 47 monitor the result. Threshold values are set such that comparator 46 returns a logic control voltage to mode control circuit 30 in the event the digital sum value rises above a predetermined higher threshold, while comparator 47 develops a similar logic control voltage in the event the sum stays below a second lower threshold value. Accordingly, comparators 46 and 47, together with their threshold settings function as a "window" comparator to develop appropriate logic control voltages in the event the digital sum value does not remain within a pre-established range or "window".

The outputs of waveform memories 39 and 40 are each coupled to a digital comparator 51 which develops a logic signal at its output to indicate when the difference between the waveforms stored in memories 39 and 40 is less than a predetermined difference ($\Delta$). The output of comparator 51 is applied to the input of a digital counter 52 which counts the number of consecutive output pulses developed by comparator 51 and provides a count-indicative output signal to mode control circuit 30. Counter 52 can be reset by means of an appropriate reset signal developed by the mode control circuit 30.

The patient's capture threshold is determined in accordance with the system and method described in the present inventor's concurrently filed copending application Ser. No. 738,609, entitled "Automatic Cardiac Capture Threshold Determination System." In determining a patient's capture threshold, the pacer control circuit 22, pacing pulse generator 23 and capture detect circuit 27 function to vary the energy of the applied pacing pulses, while simultaneously monitoring the response of the heart, in order to identify the minimum pacing pulse energy required to reliably stimulate contractions of the heart.

To develop the digitally encoded instructions for setting the energy of the pacing pulses, the pacer control circuit 22 includes a pair of data registers 52 and 53 which store a pair of variables $X_L$ and $X_H$ respectively. Variable $X_L$ represents a low pulse energy level which is generally insufficient to induce cardiac contraction while variable $X_H$ represents an energy level which is sufficiently high to reliably stimulate contractions of the heart. The system further includes a digital averaging circuit 54 for computing the arithmetic average of the $X_L$ and $X_H$ variables, as well as an additional register 55 for storing the arithmetic average so computed. A digital comparator 56, coupled to the outputs of registers 52 and 53, is also provided for comparing the $X_L$ and $X_H$ variables.

As further illustrated, the system also includes a read only memory (ROM) 57 having five memory locations 58–62 in which five constants $C_1$–$C_5$ are stored. Each of the constants can be retrieved from ROM 57 under the direction of the pacing and threshold determination control circuit 50, which also controls the input and output of data from registers 52, 53 and 55.

The outputs of registers 53 and 55, as well as the output of ROM space 61, are coupled through a three input data switch 62 to the input of a pulse level register 63. The output of register 63 is coupled through a two-position data switch 64 to the pacing pulse generator 23. Accordingly, the energy of the generated pacing pulses is determined by the value stored in the pulse level register 63. The source of the pulse level variable stored in register 63 can be either register 53 ($X_H$), register 55 (AVG), or ROM space 61($C_4$), and is determined by the position of data switch 62 under the control of the pacing and threshold determination control circuit 50.

Figure 4:
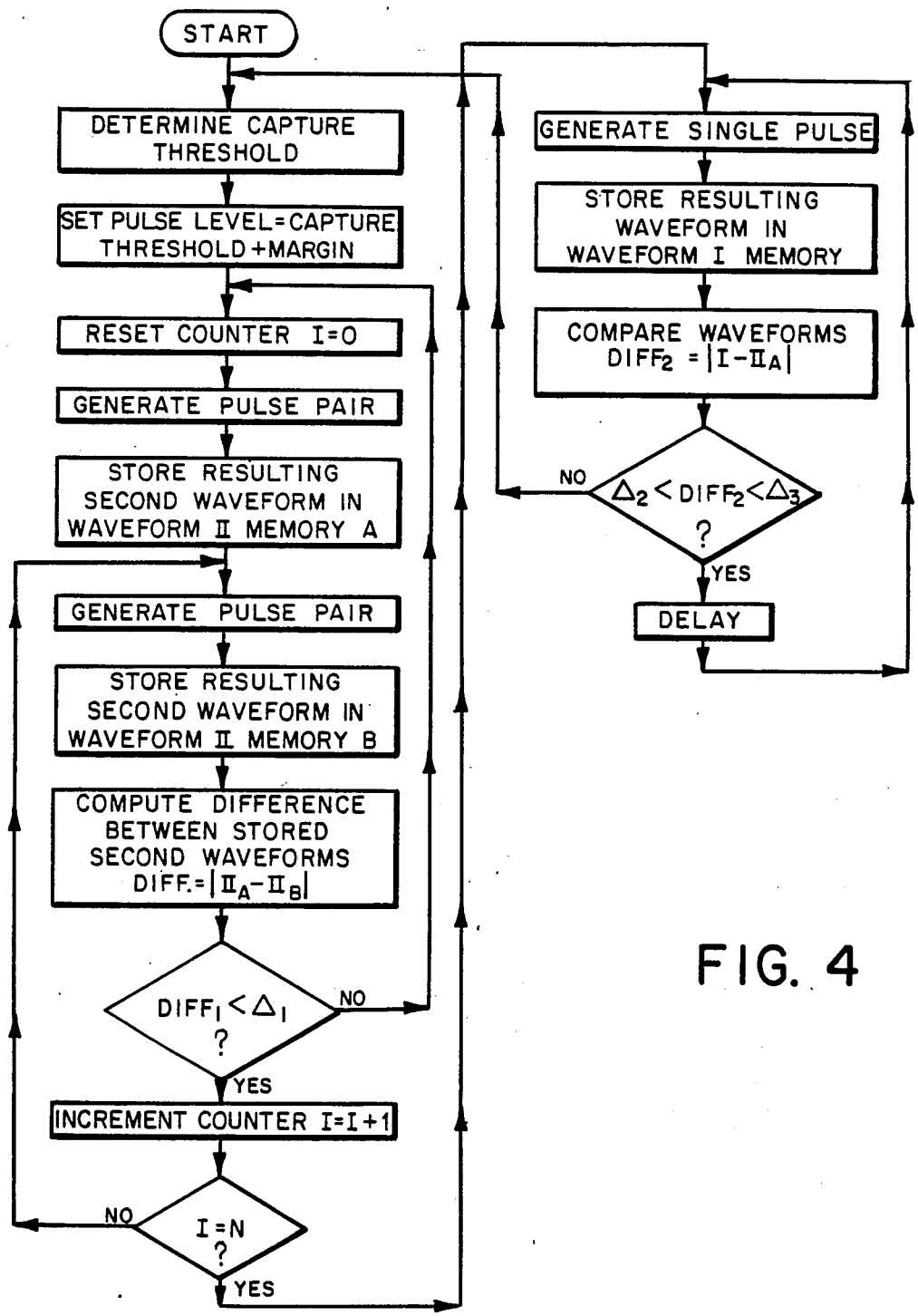
FIG. 4 is a logic flow diagram useful in understanding the operation of the improved system illustrated in FIG. 3

The operation of the pacer can be understood by reference to the block diagram of FIG. 3 and the logic flow diagram of FIG. 4. Upon receipt of a start command, the pacing and threshold determination control circuit 50 causes predetermined constant $C_1$ to be loaded into $X_L$ register 52 while constant $C_2$ is loaded into $X_H$ register 53. $C_1$ represents a pacing energy level at which cardiac capture is statistically unlikely to occur and for convenience may be set equal to zero. Constant $C_2$ represents a pulse energy level at which capture is statistically likely to occur and is preferably empirically derived.

Following such initialization of the $X_L$ and $X_H$ variables, the content of register 53 is loaded through data switch 62 into the pulse level register 63 and from there to pulse generator 23. Accordingly, the initial pacing pulse energy level will correspond to that of constant $C_2$. A pacing pulse pair at the $C_2$ energy level is then generated after which capture detect circuit 27 determines whether an induced cardiac contraction has occurred.

In the event capture does not occur at the $C_2$ pulse energy level, constant $C_2$ is loaded into the $X_L$ register 52 while constant $C_3$ in ROM space 60 is loaded into the $X_H$ register 53. The updated content of register 53 is then loaded into the pulse level register 63 with the result that pulse generator 23 is set to a new energy level corresponding to constant $C_3$. Constant $C_3$ represents a greater energy level than constant $C_2$ and has been circuit 50 causes the content of AVG register 55 to be loaded into $X_L$ register 52 with the result that variable $X_L$ is increased to the currently existing AVG level. A new average, using the updated value of $X_L$, is then computed and loaded into AVG register 55 after which a pulse pair at the new AVG energy level is generated. In the event capture is still not detected, $X_L$ is once again updated to the current AVG value, after which the average is once again recalculated. In the event three consecutive pulse pairs are generated and capture is not detected, the system generates a pulse pair at $X_H$ in order to provide patient support and to verify capture at $X_H$.

In the event the AVG energy level is sufficient to cause cardiac capture, pacing pulse energy will be reduced until capture no longer occurs. This is accomplished by loading the content of AVG register 55 into $X_H$ register 53 in order to decrease variable $X_H$ to the then existing value of variable AVG. The average is then recomputed using the new $X_H$ value and the result loaded into AVG register 55. A pulse at the new AVG energy level is generated and the response of the heart noted. In the event capture still occurs, the pulse energy level is once again reduced in the same manner. It will be noted that reducing $X_H$ is inherently safer than increasing $X_L$ since, as the pacing level is reduced, the patient's heart will continue to be paced.

Prior to setting $X_H$ equal to AVG, digital comparator 56 determines the difference between the respective values of $X_H$ and $X_L$. If $X_H$ and $X_L$ differ by less than a predetermined amount, it can be assumed that variable AVG will be substantially equal to the actual capture threshold. For safety and reliability however, variable $X_H$ is preferably selected as the capture threshold. Accordingly, when $X_H$ and $X_L$ differ by less than the predetermined amount, digital comparator 56 returns a "TEST COMPLETE" control signal to control circuit 50. Preferably, this occurs when the difference between $X_H$ and $X_L$ equals the minimum incremental pulse level change (i.e., resolution) available from pacing pulse generator 23.

The operation of the pacer, and in particular the improved capture detect circuit 27, can be understood by further reference to FIG. 3 and the logic flow diagram of FIG. 4. Upon receiving a start command, the pacing and threshold determination control circuit 50 initiates an automatic capture threshold determination cycle in which the minimum pulse energy required to reliably stimulate cardiac capture is determined. Once this energy level is determined, a "safety margin" corresponding to constant $C_5$ is added by means of an adder 65 and pacing pulse generator 23 is set to generate pacing pulses having an energy level corresponding to the capture threshold ($X_H$) plus the safety margin ($C_5$).

Next, mode control circuit 30 resets counter 52 after which a pacing pulse pair is generated by pulse generator 23 and applied to the heart. The cardiac lead response waveform developed in response to the first pulse of the pulse pair is digitized and stored in waveform I memory 38. The cardiac lead response waveform developed in response to the second pulse of the pair is digitized and stored in waveform IIa memory 39. Next, another pulse pair is generated and the digitized lead response waveform produced by the first pulse of the pair is once again loaded into waveform I memory 38. However, data switch 41 is switched such that the cardiac lead response waveform developed by the second pulse is no stored in waveform IIb memory 40. Accordingly, the lead response waveforms induced by the second pulses of two consecutive pulse pairs will be stored in waveform IIa and IIb memories 39 and 40, respectively.

Comparator 51 then compares the waveforms stored in memories 39 and 40 to develop a difference signal equal to the absolute difference between the stored lead response waveforms. In the event the difference s generated is less than some predetermined difference $\Delta_1$, counter 52 is incremented. If the total count is less than a predetermined stability index, N, another pulse pair is generated and the waveform resulting from the second pulse of the new pair is stored in waveform IIb memory 40 and 15 compared against the waveform which was developed in response to the second pulse of the first generated pulse pair and which is still stored in waveform IIa memory 39. Provided the difference between the waveforms continues to be less than Δ₁, the counter will continue to be incremented until such time as the count equals the predetermined stability index number N.

In the event any difference signal exceeds $\Delta_1$, the counter is reset and waveform memories 38, 39 and 40 are each loaded anew with appropriate waveforms developed during two consecutive applications of pulse pairs to the heart. Operation in this cycle will continue until such time as the difference is less than $\Delta_1$ indicating that the waveforms produced in response to the second pulse of each pulse pair are substantially identical.

When the count in counter 52 reaches the predetermined stability index number N, it can be assumed that the waveforms produced in response to the second pulse of each pair are substantially identical and accordingly, no new information is contained in these waveforms. Thus, when this condition is reached, the second pulse of each pulse pair serves no further useful purpose.

Accordingly, once the count in counter 52 reaches N, the mode control circuit 30 conditions pulse generator 23 to develop single pacing pulses rather than the paired pacing pulses produced up to this point. The mode control circuit 30 also develops a control signal which, in conjunction with AND gate 42, inhibits further switching of data switch 37 and causes the output of ADC 36 to be continuously coupled to waveform I memory 38. Accordingly, upon the generation of each single pacing pulse, the resulting cardiac response waveform will be stored in waveform I memory 38. Waveform IIa memory 39 however will continue to store a waveform produced in response to the second pulse of one of the earlier generated paired pulses and will be available as a "template" for comparison against the waveforms coming into memory 38. Subtractor 43 continually processes the incoming lead response waveforms in memory 38 and the stored template waveform in memory 39, developing a signal indicative of the difference between the two waveforms. This difference signal is integrated in digital integrator 44 over a predetermined number of bytes, which corresponds to a specific time interval. If this integration value is between the limits established by the "window" comparators 46 and 47, single pacing pulses will continue to be generated at a rate consistent with the desired cardiac pulse rate.

In the event the integrated value falls outside these limits, it it can be assumed that either capture has been lost or the stored waveform in waveform memory 39 is no longer an accurate representation of the lead recovery response artifact. Accordingly, when this occurs, pulses are once again generated in pairs and the acquisition of a new lead recovery artifact template is thereafter obtained.

It will be appreciated that while discrete system components, such as the various registers, comparators, and control circuits have been shown and described, the system may be advantageously implemented using microprocessor-based circuitry in conjunction with suitable programming. Additionally, it will be appreciated that variation of the pacing energy level can be accomplished through variation of either or both of the pacing pulse amplitude and pulse duration. Furthermore, it will be appreciated that while various constants have been identified and described, these constants can be adjusted to suit the particular needs of individual patients without departing from the scope of the invention.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

I claim:

1. A system for detecting the responsiveness of a patient heart having a predetermined minimum refractory period to pacing pulses having a predetermined energy level, comprising:
    generating means electrically coupled to the heart for generating a series of pacing event signals, each comprising in a first mode a pair of pulses of the predetermined energy level and separated in time by less than the refractory period of the heart, and in a second mode each comprising a single pulse of the predetermined energy level;
    detection means electrically coupled to the heart for detecting the artifact signals produced by the heart in response to each of said pacer pulses;
    storage means for storing the one of said artifact signals corresponding to the one of said individual pulses in said event which did not induce a cardiac event;
    means for conditioning said generating means to said second mode to develop single pulse pacing events following storage of said one artifact signal;
    comparison means for compariang the artifact produced in response to each of said single pacing pulses in said second mode of said generating means with said one artifact signal in said storage means to produce a difference signal indicative of a response by the heart to said pacing events.

2. A system for detecting evoked cardiac contractions as defined in claim 1 including a pacing lead for coupling said generating means to the heart and the heart to said detection means.

3. A system for detecting evoked cardiac contractions as defined in claim 1 wherein said comparison means subtract the absolute values of said single pulse artifacts with said stored pulse artifact signals following each pacing event to develop a diference signal indicative of capture occurrence.

4. A system for detecting evoked cardiac contractions as defined in claim 3 wherein said comparison means include threshold means for producing an output when said difference signal exceeds a predetermined threshold level.

5. A system for detecting evoked cardiac contractions as defined in claim 4 wherein said comparison means include integrating means for integrating said difference signal to develop a signal for application to said threshold means.

6. A system for detecting evoked cardiac contractions as defined in claim 4 including a pacing lead for coupling said generating means to the heart and the heart to said detection means.

7. A system for detecting evoked cardiac contractions as defined in claim 1 wherein said pacing pulses are of equal amplitude.

8. A system for detecting evoked cardiac contractions as defined in claim 1 including window comparator means for comparing said difference single against upper and lower limits, and for storing said one of said artifacts when said difference signal falls outside of said limits.

9. A system for detecting evoked cardiac contractions as defined in claim 8 wherein said pacing pulses are of equal amplitude.

10. A system for detecting the responsiveness of a patient heart having a predetermined minimum refractory period to pacing pulses having a predetermined energy level, comprising:
   generating means electrically coupled to the heart for generating a series of pacing event signals, each comprising in a first mode a pair of pulses of the predetermined energy level and separated in time by less than the refractory period of the heart, and in a second mode each comprising a single pulse of the predetermined energy level;
   detection means electrically coupled to the heart for detecting the artifact signals produced by the heart in response to each of said pacer pulses;
   storage means for storing the one of said artifact signals corresponding to the one of said individual pulses in said event which did not induce a cardiac event;
   subtraction means for subtracting following each pacing event the absolute values of the artifact signal stored in said storage means with the artifact produced in response to each such single pacing pulse to develop a difference signal;
   integrating means for integrating said difference signal to develop an integrated difference signal; and
   output circuit means for providing an output signal indicative of capture when said integrated difference signal exceeds a predetermined threshold level.

11. A system for detecting evoked cardiac contractions as defined in claim 10 wherein said pacing pulses are of equal amplitude.

12. A method for detecting cardiac contractions induced in response to the application of pacing pulses to a patient's heart having a predetermined minimum refractory period, comprising the steps of:
   applying a first pacing pulse to the patient's heart;
   detecting a first recvery artifact, indicative of cardiac activity, produced in response to application of said first pulse to the patient's heart;
   applying, in an alternate mode of operation, a second pacing pulse to the patient's heart within a time period following the application of said first pulse which is less than the minimum refractory period of the patient's heart;
   detecting the recovery artifact, indicative of cardiac activity, product in response to application of said second pulse to the patient's heart;
   storing the artifact signal corresponding to said second pacing pulse upon said first pacing pulse evoking capture;
   conditioning said generating means to said alternate mode to develop only said first pacing pulse following storing of the artifact signal; and
   comparing the artifact produced in response to each of the single pacing pulses with the stored artifact signal to produce a difference signal indicative of a response by the heart to such single pacing signal.

13. The method of detecting induced cardiac contractions defined in claim 12 wherein said comparing said first and second recovery artifact signals comprises developing a different signal indicative of the difference between the absolute values of said artifact signals, integrating the different signal, comparing the integrated difference signal with a threshold signal level, and providing an output signal indicative of capture upon the integrated difference signal exceeding the threshold level.

* * * * *

UNITED STATES PATENT AND TRADEMARK OFFICE
CERTIFICATE OF CORRECTION

PATENT NO. : 4,674,508
DATED : June 23, 1987
INVENTOR(S) : Robert DeCote, Jr.

It is certified that error appears in the above-identified patent and that said Letters Patent are hereby corrected as shown below:

ABSTRACT, Line 13: Change "supplied" to --applied--.

Col. 5, line 32: Change "an" to --and--.

Col. 7, line 29: Change "$C_1$" to --$C_1$--.

Col. 8, line 53: Change "no" to --now--.

line 61: Change "s" to --so--.

Col. 9, line 3: "Change "$\Delta_1$" to -- $\Delta_1$--.

Signed and Sealed this

Twenty-fourth Day of November, 1987

Attest:

DONALD J. QUIGG

*Attesting Officer*  *Commissioner of Patents and Trademarks*